United States Patent
Schwägli et al.

(10) Patent No.: US 10,987,148 B2
(45) Date of Patent: Apr. 27, 2021

(54) BONE CLAMP WITH ADAPTER FOR MEASUREMENT AIDS

(71) Applicant: Naviswiss AG, Brugg (CH)

(72) Inventors: Tobias Schwägli, Solothurn (CH); Jan Stifter, Schweiz (CH); Thomas Hauri, Gränichen (CH)

(73) Assignee: Naviswiss AG, Brugg (CH)

( * ) Notice: Subject to any disclaimer, the term of this patent is extended or adjusted under 35 U.S.C. 154(b) by 233 days.

(21) Appl. No.: 16/328,622

(22) PCT Filed: Sep. 1, 2017

(86) PCT No.: PCT/EP2017/071935
§ 371 (c)(1),
(2) Date: Feb. 26, 2019

(87) PCT Pub. No.: WO2018/041984
PCT Pub. Date: Mar. 8, 2018

(65) Prior Publication Data
US 2021/0038276 A1   Feb. 11, 2021

(30) Foreign Application Priority Data
Sep. 2, 2016   (CH) ................... 01138/16

(51) Int. Cl.
*A61B 17/88* (2006.01)
*A61B 17/86* (2006.01)
(Continued)

(52) U.S. Cl.
CPC ...... *A61B 17/8866* (2013.01); *A61B 17/7047* (2013.01); *A61B 17/8076* (2013.01);
(Continued)

(58) Field of Classification Search
CPC ..... A61B 17/8866; A61B 90/57; A61B 90/10; A61B 17/8009; A61B 17/7047; A61B 17/8076
See application file for complete search history.

(56) References Cited

U.S. PATENT DOCUMENTS

| 5,807,252 A | 9/1998 | Hassfeld |
| 6,711,431 B2 | 3/2004 | Sarin |

(Continued)

FOREIGN PATENT DOCUMENTS

| DE | 102006035602 A1 | 2/2008 |
| EP | 1779798 A1 | 5/2007 |
| EP | 1872733 A1 | 1/2008 |

OTHER PUBLICATIONS

International Search Report for PCT/EP2017/071935, dated Oct. 27, 2017, 6 pages.
(Continued)

*Primary Examiner* — Andrew Yang
(74) *Attorney, Agent, or Firm* — Hard IP LLC

(57) ABSTRACT

A bone clamp for securing of a measurement aid to a bone comprises a first clip and a second clip and an adapter. The adapter comprises a pulling mechanism and a locking mechanism, whereby the position of the first clip relative to the second clip can be altered by actuation of the pulling mechanism, wherein the position of the first clip relative to the second clip can be fixed by actuation of the locking mechanism. The first clip and the second clip each have an inner face which is oriented in the direction of the bone, wherein the first clip has one or more spikes on the inner face and wherein the second clip has a sliding edge on the inner face.

20 Claims, 10 Drawing Sheets

(51) Int. Cl.
  *A61B 90/57* (2016.01)
  *A61B 17/80* (2006.01)
  *A61B 17/70* (2006.01)
  *A61B 90/10* (2016.01)
  *A61B 34/10* (2016.01)
  *A61B 90/00* (2016.01)
  *A61B 17/00* (2006.01)

(52) U.S. Cl.
  CPC .......... *A61B 17/8605* (2013.01); *A61B 90/10* (2016.02); *A61B 90/57* (2016.02); *A61B 17/8009* (2013.01); *A61B 34/10* (2016.02); *A61B 2017/00486* (2013.01); *A61B 2090/066* (2016.02)

(56) References Cited

U.S. PATENT DOCUMENTS

| | | |
|---|---|---|
| 8,002,772 B2 | 8/2011 | Sarin |
| 2006/0100638 A1 | 5/2006 | Sarin |
| 2008/0027471 A1 | 1/2008 | Hauri et al. |
| 2015/0038836 A1 | 2/2015 | Hladio et al. |
| 2015/0327937 A1* | 11/2015 | Schuele ................ A61B 90/16 606/59 |

OTHER PUBLICATIONS

International Preliminary Report on Patentability Chapter I for PCT/EP2017/071935, dated Mar. 5, 2019, 13 pages.

\* cited by examiner

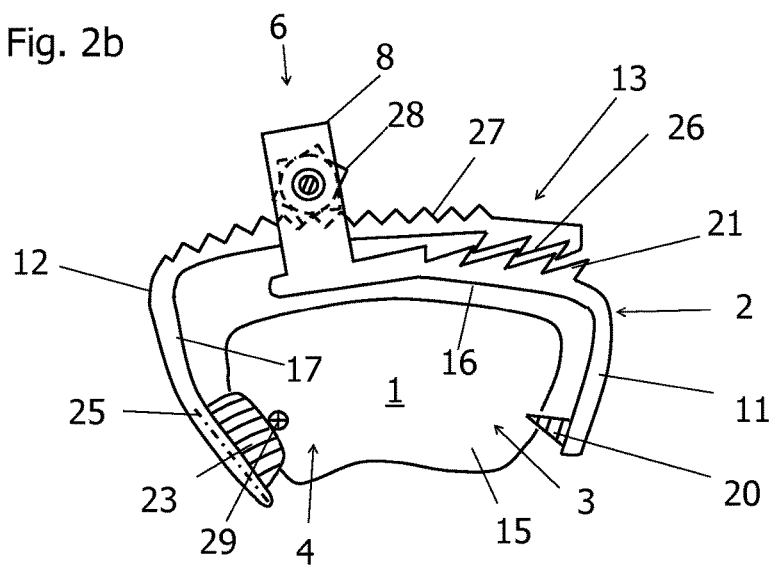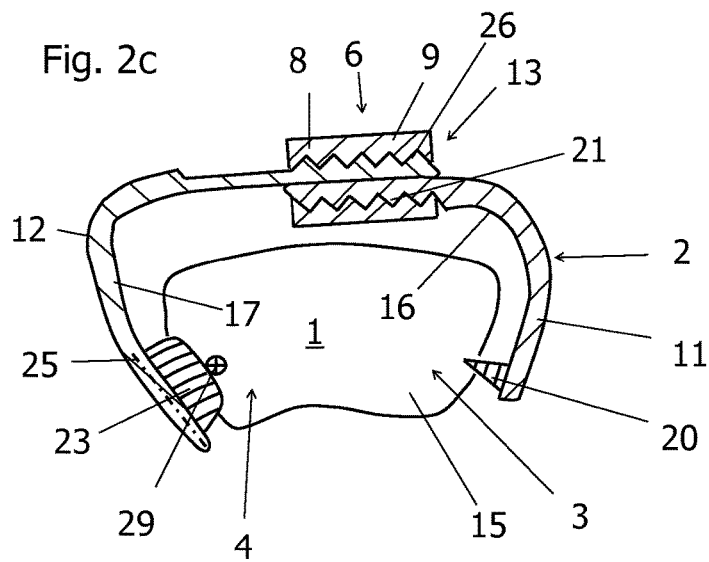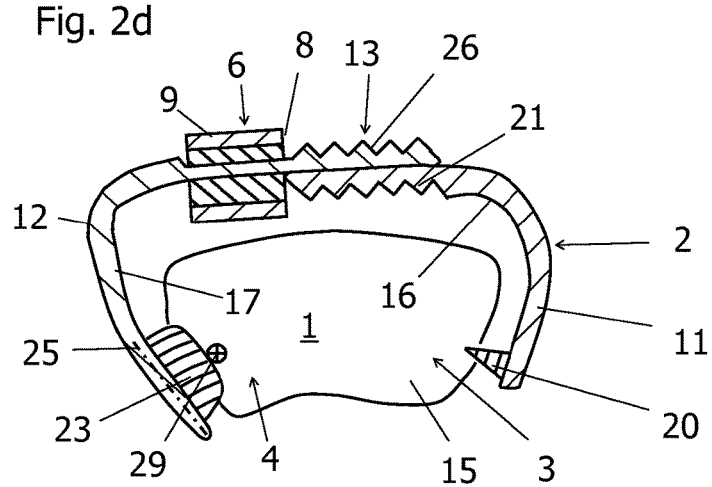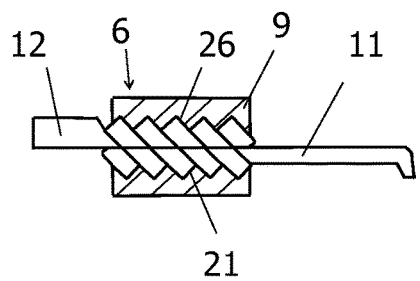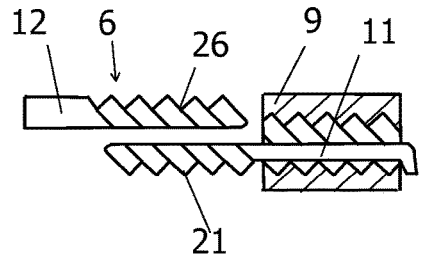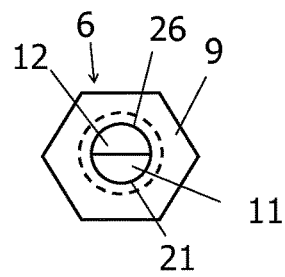

Fig. 13
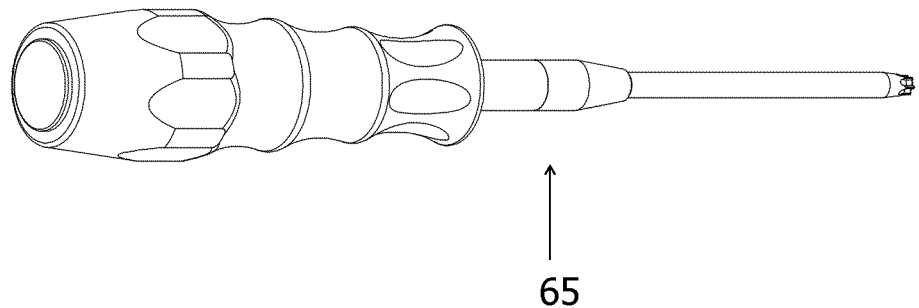
Fig. 14b
Fig. 14a
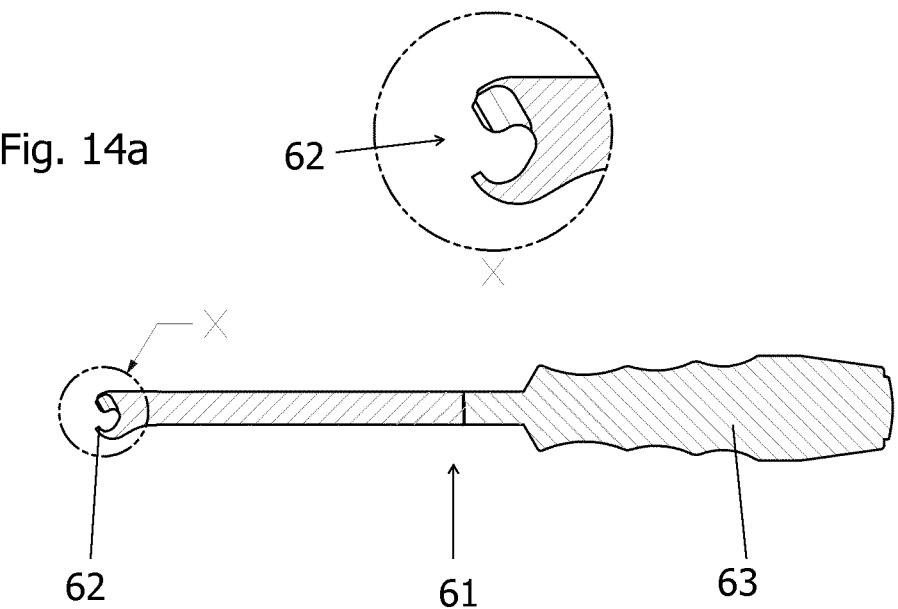
Fig. 15
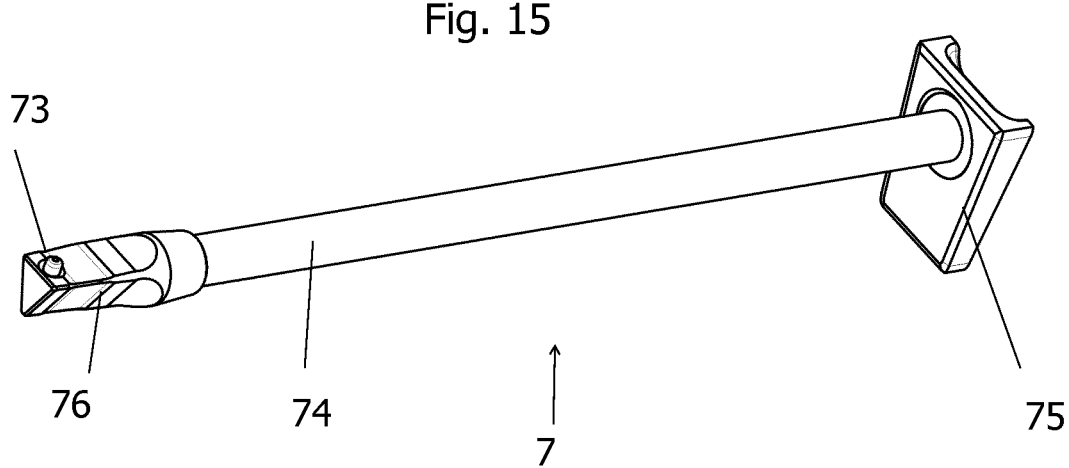

BONE CLAMP WITH ADAPTER FOR MEASUREMENT AIDS

CROSS-REFERENCE TO RELATED APPLICATIONS

This application is a U.S. national stage filing under 35 U.S.C. 371 of international patent application no. PCT/EP2017/071935, filed on Sep. 1, 2017, which claims priority to Swiss patent application no. CH01138/16, filed on Sep. 2, 2016, the contents of both of which are incorporated herein by reference in their entirety.

TECHNICAL FIELD

The invention relates to a bone clamp, in particular a surgical bone clamp, which is equipped with an adapter for a measurement aid for computer-assisted surgery. The invention also relates to a system comprising a bone clamp and a measurement aid.

Important demands on such bone-mounted bone clamps are that the measurement aid maintains a constant geometric reference to the bone during the surgical procedure and that the attached bone clamp does not interfere with the surgical procedure. In particular, minimally invasive procedures place high demands on the design and ergonomics of a bone clamp and measurement aids.

In each case, a fixed geometric reference of the measurement aid to the bone is sought. Force effects on the measurement aid, such as unintentional abutment by the surgeon, must neither change the position of the measurement aid nor impair its attachment in or on the bone. Acting forces on measurement aids on long lever arms can generate large torques and thus allow large forces to act on the screwed connections in the bone material. Especially with minimally invasive procedures, the space available for the measurement aid is limited, which increases the risk of unintentional collisions. The bone clamp must therefore lie as flat as possible on the bone.

DESCRIPTION OF RELATED ART

The state of the art for the attachment of a measurement aid to a bone, in particular in the area of the femoral neck bone in a hip joint operation, can be described with reference to the following disclosure and patent documents.

U.S. Pat. No. 5,807,252 [Aesculap AG] describes a bone screw and US 20150038836 A1 [Intellijoint Survivals Inc.] describes a screwed mounting device for a measurement aid, which is screwed to the bone at a suitable location directly or by means of an adapter. A disadvantage of this type of fastening technique is that relatively large forces can act on the screw connection or the bone material that can be generated, for example, in a collision with the measurement aid, for example, by an accidental abutment on the measurement aid. The screw connection must therefore be dimensioned correspondingly massively, which also results in a large altitude with respect to the bone.

US2008/0027471 A1 [Hauri] describes a clamp with at least two mutually movable jaw parts, which is clamped to the bone. The clamping mechanism consists of interlocking sawtooth-shaped surfaces. The necessary force is generated by a pair of pliers. The actual secure fit on the bone is made possible by spikes or other sharp structures on the clamp, which are pressed into the bone surface by the clamping process. In this case too, large forces can act locally on the bone. Minimally invasive interventions may not provide the necessary space. In addition, it is difficult to put this clamp flat on the bone, since the clamp cannot adapt to the bone when contracting.

U.S. Pat. No. 8,002,772 B2 [Kinamed, Inc] describes a clamp with two mutually movable toothed jaw parts, which are clamped to the bone by means of an integrated threaded rod. Thanks to the jaw parts rotatable about axes of rotation, the clamp can adapt to the surface topology of the bone. Spikes or other sharp structures, which are pressed into the bone surface by the clamping process, allow a secure fit of the clamp on the bone. The local force on the bones can be relatively large when clamping.

U.S. Pat. No. 6,711,431 B2 [Kinamed Inc.] describes a stiff collar that is temporarily attached to the large trochanter at the femur by means of strings. The strings are wrapped around the femur. At this collar measuring means are attached. This attachment method protects the bone.

SUMMARY OF THE INVENTION

The object of the present invention is to further develop bone-fixed bone clamps for surgery in such a way that firstly, the forces of the clamp acting on the bone are optimally distributed, secondly, the bone clamp can attach well to the bone structure when closing, thirdly, the injury to the bone and the surrounding tissue are limited to a minimum and fourthly, measurement aids do not get in the way of the attending physician when performing the operation. In addition, the attachment and removal of the clamp on the bone should take ergonomic aspects into account and the fastened clamp should not interfere with accessibility during surgery, particularly minimally invasive surgery.

The object is solved by the features of the claims. Advantageous developments are subject of the dependent claims. The advantage of the invention is that the proposed surgical bone clamp comprises a relatively large proportion of the bone circumference, that the bone clamp itself centers around the bone when it is fixed, and that the bone clamp has a small height relative to the bone surface.

When the term "for example" is used in the following description, this term refers to embodiments and/or variants, which is not necessarily to be understood as a more preferred application of the teachings of the invention. Similarly, the terms "preferable", "preferred" are to be understood by referring to an example of a set of embodiments and/or variants, which is not necessarily to be understood as a preferred application of the teachings of the invention. Accordingly, the terms "for example," "preferred," or "preferred," may refer to a plurality of embodiments and/or variants.

The following detailed description contains various embodiments of the inventive bone clamp. The description of a particular bone clamp is to be considered as exemplary only. In the specification and claims, the terms "contain," "include," "comprise" are interpreted as "including, but not limited to."

A bone clamp for attaching measurement aids to a bone includes a first and a second clip and an adapter. The adapter includes a pulling mechanism and a locking mechanism. By actuating the pulling mechanism, the position of the first clip relative to the second clip is changeable. By operating the pulling mechanism or the locking mechanism, the position of the first clip relative to the second clip can be fixed. The first and second clips each have an inner face which is oriented in the direction of a bone surface of the bone. The first clip contains one or more spikes on the inside. The second clip contains a sliding edge on the inside. By means of a spike, a substantially punctiform support on the bone surface can be realized. By means of a sliding edge, a linear or planar support on the bone surface can be realized.

According to an embodiment, the second clip has a clip axis, wherein the sliding edge is arranged parallel to the clip axis. In particular, the sliding edge can be designed as a cutting edge extending parallel to the clip axis. A sliding edge may be mounted on the first clip at a distance from the spike.

The first clip may have a clip axis, wherein the sliding edge is arranged parallel to the clip axis. According to one embodiment, the two sliding edges can be parallel to the corresponding clip axes. According to an embodiment, the two sliding edges and the spike may lie in the same plane. The sliding edges can enclose an angle smaller than 90° to each other.

In an embodiment, at least one of the first and second clips may be shaped to partially enclose the bone.

According to an embodiment, at least one of the first or second clips may be designed to be at least partially flexible. In particular, the first clip can be connected to the second clip via an adapter which is designed as a flexible clip element. Alternatively, in addition to the adapter, a flexible clip element may be formed on one of the first or second clips.

According to an embodiment, the locking mechanism comprises first and second sawtooth-like structures, which are arranged on the first and second clip and are intended for mutual engagement.

According to an embodiment, the pulling mechanism comprises a gear arranged on the first clip and a rack disposed on the second clip, the rack and the gear being intended for mutual engagement. According to an embodiment, the gear may be removably mounted on the first clip.

According to an embodiment, the adapter includes a fastening device for a measurement aid. The attachment device for the measurement aid may be removable from the first clip. In particular, the measurement aid can be temporarily fixed for measuring purposes on the bone clamp in a geometrically defined manner by means of adapters. At least one eyelet for a bone screw may be provided on at least one of the first and second clips. The eyelet can be designed to receive a head locking screw.

According to an embodiment, the force of the first and second clips can be adjusted to the bone by means of a torque measurement device. The torque measurement device may be attached to the pulling mechanism.

According to an embodiment, a plurality of spikes can form a spike group.

According to any one of the embodiments, at least one of the sliding edges can include a plurality of cutting edges, wherein the cutting edges of the sliding edge form a group of cutting edges.

A system according to any one of the embodiments comprises a bone clamp comprising an adapter containing a measurement aid. The measurement aid may be releasably attached to the adapter and extending at least over the tissue surface of the patient or protruding beyond the tissue surface of the patient. In particular, the measurement aid has a longitudinal dimension which extends from the surface of the first or second clip to the end of the measurement aid and forms a first lever arm. A second lever arm may extend from the surface of the first or second clip to the projection point of the track center of the sliding edge. Advantageously, the ratio of the length dimensions of the first lever arm to the second lever arm is a maximum of five. According to a preferred embodiment, the ratio of the length dimensions of the first lever arm to the second lever arm is a maximum of four. According to a particularly preferred embodiment, the ratio of the length dimensions of the first lever arm to the second lever arm is a maximum of three, thus, the first lever arm is substantially three times longer than the second lever arm.

The proposed bone clamp according to one of the preceding embodiments can in particular encompass a relatively large proportion of the bone circumference. The bone clamp can be stably aligned by the spike and the sliding edge or the sliding edges on the inside of the bone. The bone clamp has a very small height with respect to the bone surface because of the detachable adapter.

BRIEF DESCRIPTION OF THE DRAWINGS

The invention will be explained in more detail with reference to an embodiment of a bone clamp on the femur for a hip operation, which is illustrated in the drawings.

It is shown in:

FIG. 2b is a side view of a second embodiment of a bone clamp,

FIG. 2c is a side view of a third embodiment of a bone clamp,

FIG. 2d is the bone clamp according to FIG. 2c,

FIG. 2e is a detail of the adapter of the bone clamp according to FIG. 2c,

FIG. 2f is a detail of the adapter of the bone clamp according to FIG. 2c,

FIG. 2g is a sectional view of the adapter of the bone clamp according to FIG. 2c, FIG. 13 is a view of a coupling tool, FIG. 14a is a view of an unlocking tool, FIG. 14b is a detail of FIG. 14a, and FIG. 15 is an embodiment of a holding element for a measurement aid.

DETAILED DESCRIPTION

Figure 1:
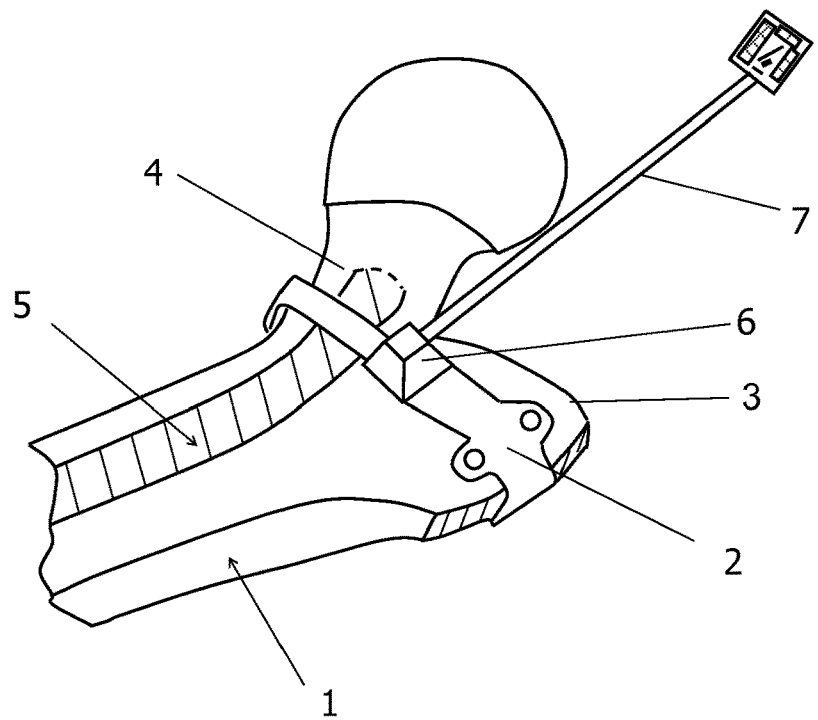
FIG. 1 is an outline sketch of a bone clamp.

FIG. 1 shows an outline sketch of an application example of a bone clamp 2 using the example of a femur 1 with the essential elements of a bone clamp 2 with a measurement aid 7 mounted on an adapter 6 for a hip operation. The bone clamp 2 is located at the level of the of line femoral neck 4 to the large trochanter 3, i.e. in the leg region of the femoral neck 4. The region 5 for a femoral prosthesis to be implanted is shown in dashed lines. No additional fixing screws may be placed in this region 5.

Figure 2A:
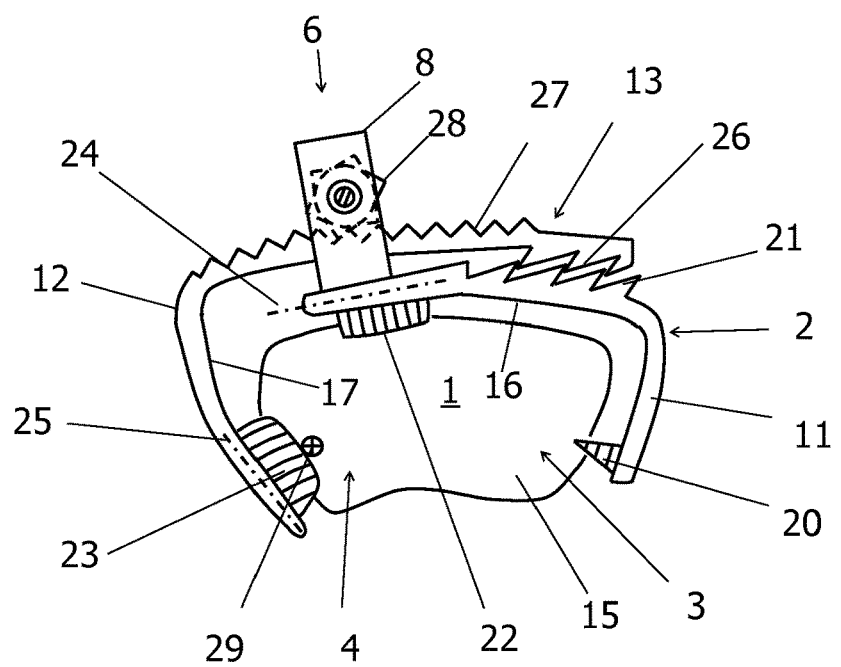
FIG. 2a is a side view of a first embodiment of a bone clamp.

The positioning of the bone clamp 2 is accomplished by a suitable setting instrument, with which the bone clamp 2 can be held and placed in position, which is not shown in the drawing. Preferably, the pulling mechanism 8 or the locking mechanism 13 of the bone clamp 2, as shown in FIG. 2a, can be actuated via this setting instrument. The bone clamp 2 is preferably designed such that it does not have to be placed over soft tissue structures.

For example, the measurement aid 7 may comprise a marking element and a rod element. The rod element may for example have a length of about 11 cm. The marking element may for example have a substantially rectangular shape. According to an embodiment, the length of the rectangle is approximately 2.5 cm. The width of the rectangle is approximately 2.5 cm.

FIG. 2a shows the side view of a first exemplary embodiment of a bone clamp 2, which is arranged in cross-section 15 of a femur at the height of the large trochanter 3 and the femoral neck 4. The bone clamp 2 consists essentially of the two first and second clips 11 and 12 and an adapter 6. A spike 20 is positioned at the edge of the free end of the first clip 11 on the inside of the first clip 11. A pulling mechanism 8 for fixing the bone clamp 2 to the bone is arranged at the other end of the first clip 11. The pulling mechanism 8 causes a contraction of the bone clamp, whereby the bone clamp can be held on the bone. An area with first sawtooth-like structures 21 is arranged on the outside of the first clip 11 for fixing purposes. A sliding edge 22 is arranged below the pulling mechanism 8 parallel to the clip axis 24 of the first clip 11. A sliding edge 23 is also attached at the edge of the second clip 12 parallel to the clip axis 25 of the clip 12. An area with second sawtooth-like structures 26 is arranged on the inside of the second clip 12. The top of the second clip 12 is formed as a rack 27 for the gear 28 of the pulling mechanism 8. The gear 28 is rotated, for example, with a suitable screwdriver, which is not shown in the figure. This pulling mechanism 8 is preferably also used as a setting tool of the bone clamp. The two clips 11, 12 are held together by guide mechanisms in the unassembled state which is not shown in the figure.

The pulling mechanism 8 can be removed as needed from the bone clamp 2, thereby freeing this space for the surgeon.

Instead of the pulling mechanism 8, a device for mounting the measurement aid can be mounted. Depending on the design of the adapter 6 more than one measurement aid can be attached to the device. Also, this adapter 6 or the measurement aid can be temporarily removed as needed. It is important that the adapter 6 can be re-attached to the attached bone clamp 2, so that the same geometric reference of the measurement aid is restored with respect to the bone. The adapter 6 for attaching the measurement aids can simultaneously also contain the pulling mechanism 8 of the bone clamp 2. The adapter 6 for the measurement aids may be mounted at another suitable location, in particular not directly at the pulling mechanism 8.

In the following, the attachment of the bone clamp 2 will be described. The surgeon places the bone clamp 2 on the bone as indicated in FIGS. 1 and 2, for example over the exposed part of the femur, so that the spike 20 of the first clip 11 bears against the bone surface. By means of the pulling mechanism 8, the second clip 12 is pulled towards the bone surface. Alternatively, it is possible to insert the bone clamp 2 in the closed state in the surgical field and then to open it only before the attachment as previously described. In a first instance, the forces generated by the actuation of the pulling mechanism 8 cause the spike 20 to penetrate the bone surface, in a second instance, the sliding edges 22, 23 also begin to penetrate the bone surface as cuts and additionally slide along the bone surface due to the forces acting thereon. By means of the sliding edges 22, 23, it is also prevented that the bone clamp 2 slips up along the femoral neck 4 and thus cannot be fixed at the optimum position. A balance of forces is achieved as soon as the sliding edges 22, 23 no longer move and both the spike 20 and the sliding edges 22, 23 have penetrated sufficiently deep into the bone surface. The sliding edges 22, 23 may contain at least one element from the group of edges, cutting edges or ribs. The maximum acting forces can be adjusted and/or controlled by an optional torque measurement by means of a torque measuring device, for example a screwdriver or a torque wrench. In the last phase of contraction, the teeth of the first and second sawtooth-like structures 21, 26 of the locking mechanism 13 intermesh, e.g. catch, the locking mechanism 13 of the bone clamp 2 is closed when the second clip 12 rotates about the pivot point 29 at the sliding edge 23 and thus the second sawtooth-like structure 26 of the second clip 12 is positively forced into the first sawtooth-like structure 21 of the first clip 11 into it.

The result is a rigid bone clamp which, due to sufficient anchoring by the spike or spikes 20, or the sliding edges 22, 23 in the bone 1, has a fixed geometrical relation to the bone 1. The shape of the first and second clips 11, 12 is important for a tight clamping seat: the sliding edge 23 must not slide away from the bone during contraction. Therefore, the second clip 12 with the sliding edge 23 must partially surround the bone. The term "partially encompassing" should be understood in particular that at least half of the bone circumference of the first clip 11 and/or the second clip 12 is detected. In particular, the two sliding edges 22, 23, respectively, their associated clip axes 24 and 25, enclose an angle of less than 90°.

A particularly low height of the mounted bone clamp 2 is achieved by a slightly curved clamp shape, which is adapted to the bone surface. In addition, each of the first or second clips 11, 12 may be at least partially flexible. If at least one of the first or second clips 11, 12 contains a flexible material, this flexible material can adapt to the bone surface particularly well.

FIG. 2b shows a side view of a second embodiment of a bone clamp 2, which differs from the first embodiment on the one hand, in that the adapter 6 is part of at least one of the first and second clip 11, 12, and furthermore differs in that the adapter 6 from the first clip 11 is not removable. For components of the same function, the same reference numerals are used. For the components of the same function, which have already been described in connection with previous embodiments, reference is made to the description of these embodiments. The variant shown in FIG. 2b may find application when the adapter 6 is not considered to be an obstacle in the further course of the operation. The adapter 6 may also include a receiving element for a measurement aid 7, which is not shown in the drawing. The embodiment according to FIG. 2b doesn't contain a sliding edge 22. For the stabilization, the first clip 11 can partially rest on the bone surface in the state in which the locking mechanism 13 is closed, such that the bone clamp 2 is fixed stably on the bone even when omitting the sliding edge 22. According to an embodiment, not shown, the sliding edge 23 can be omitted on the second clip 12 as well, instead, the sliding edge 22 may be provided on the first clip 11.

FIG. 2c shows a side view of a third embodiment of a bone clamp 2. This embodiment differs from the previous embodiments in that the adapter 6 includes the pulling mechanism 8 and the locking mechanism 13, wherein the functions of the pulling mechanism 8 and the locking mechanism 13 are coupled. Each of the first and second clips 11, 12 contains a sawtooth-like structure 21, 26. A sawtooth-like structure is hereby representative of all forms of tooth shapes which are intended for mutual engagement. In particular, all the tooth shapes that can be used for a thread can be used. However, the sawtooth-like structures 21, 26 do not engage with each other, but are part of an external thread. As shown in FIG. 2e, the first clip 11 and the second clip 12 are provided with semi-circular cross-sections in the vicinity of the adapter 6. The sawtooth-like structures 21, 26 are threadably mounted on the outer, semi-circular surfaces of the first and second clips 11, 12. The flat surfaces of the clips 11, 12 are intended to rest upon each other, which is shown in FIGS. 2c to 2g. In the locked state, the sawtooth-like structures 21, 26 are at least largely accommodated in an internal thread of a sleeve element 9.

FIG. 2d shows the bone clamp 2 according to FIG. 2c, when the locking mechanism 13 of the adapter 6 is opened. Although the end of the first clip 11, which contains the first sawtooth-like structure 21, rests still on the end of the second clip 12, which contains the second sawtooth-like structure 26, the two clips 11, 12 are free and can be removed from the bone 1. The first and second clips 11, 12 may be subjected to a pre-tensioning in the present position which has been previously applied manually or by means of a setting element before the locking mechanism 13 had been closed.

Thus, whenever the locking mechanism 13 is released, the end of the first clip 11 can move away from the end of the second clip 12 and the sliding edge 22 and the spike 20 can be released. The clips 11, 12 of the bone clamp can be removed. The sleeve element 9 remains according to the illustration of FIG. 2d connected to the second clip 12, a recess on the second clip 12 is provided for the sleeve element 9 according to this embodiment. The sleeve element is thus removed together with the second clip 12, which simplifies handling.

Since the sleeve element 9 on the second clip 12 is free to move when the locking mechanism is open, this sleeve element can also be used as a pulling mechanism. The sleeve element 9 may be partially screwed onto the second sawtooth-like structure 26 of the second clip before the first sawtooth-like structure 21 is connected to the sleeve element 9. The sawtooth-like structures 21, 26 are thus arranged offset to one another according to this illustration. The more the two sawtooth-like structures overlap in the locked state of the locking mechanism 13, the greater the clamping force, that is, the deeper the sliding edge 23 and the spike 20 penetrate into the bone surface.

By adapting the clamping force, the bone clamp can be used for bones of different consistency, in particular different hardness. For harder bones, a greater clamping force can be selected by increasing the degree of overlap of the sawtooth-like structures. Thus, according to the present configuration, the adapter 6 can also perform the function of a pulling mechanism 8.

FIG. 2e shows a detail of the adapter 6 of the bone clamp 2 according to FIG. 2c, wherein the locking mechanism 13 of the adapter 6 is in the locked state, which corresponds to the illustration according to FIG. 2c, but in contrast to FIG. 2c the sleeve element 9 remains connected to the first clip 11, which is shown in FIG. 2f. In the illustration according to FIG. 2e, only the sleeve element 9 is shown in sectional view, the sawtooth-like structures 21, 26 of the first and second clips 11, 12 are not shown in sectional view.

FIG. 2f shows a detail of the adapter 6 of the bone clamp 2 according to FIG. 2c, the locking mechanism 13 being in the released state, which corresponds to the illustration according to FIG. 2d, with the difference that the sleeve element 9 remains connected to the first clip 11.

FIG. 2g shows a section through an adapter 6 of the bone clamp 2 according to FIG. 2c. The representation of hatching has been dispensed with in this sectional view such that the essential sub-elements of the adapter 6 come to advantage. The sleeve element 9 is disposed according to this exemplary embodiment with a hexagonal cross-sectional area, which has for example a size suitable for a wrench. Also, a cross-sectional area formed as a square or a circular cross-sectional area may be used of which at least one segment is cut away.

The first clip 11 and the second clip 12 are received in the sleeve element. The thread is schematically indicated by a dashed line. The cross sections of the first and second clip 11, 12 are semicircular according to this embodiment. If the first and second clips 11, 12 are arranged opposite one another, a circular cross-sectional area with an external thread results. The external thread of the first and second clip 11, 12 is particularly suitable for engagement with the internal thread of the sleeve element 9.

Figure 3A:
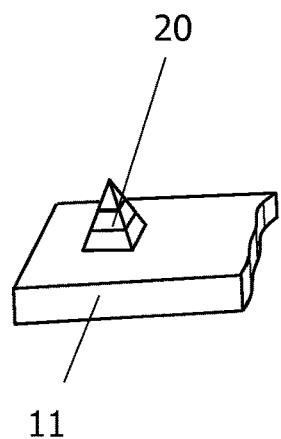
FIG. 3a is a detail of an arrangement of a spike.
Figure 3B:
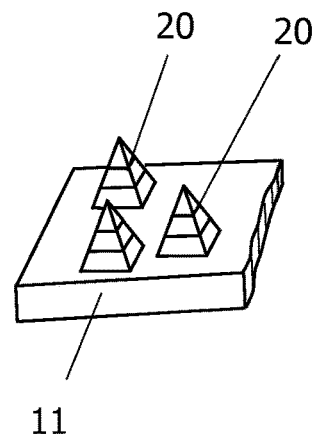
FIG. 3b is a detail of an arrangement of a spike group.
Figure 4A:
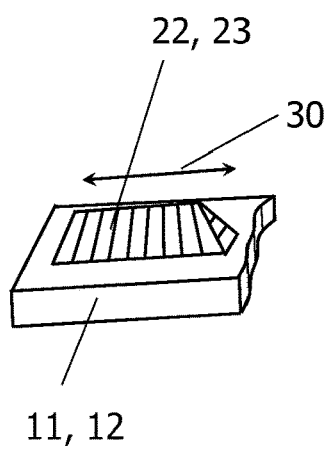
FIG. 4a is a detail of a first embodiment of a sliding edge.
Figure 4B:
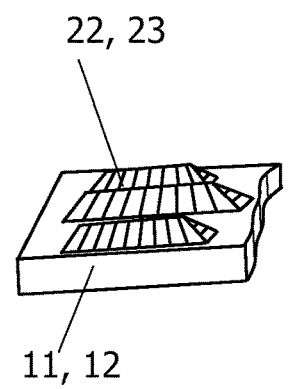
FIG. 4b is a detail of a cutting group.
Figure 4C:
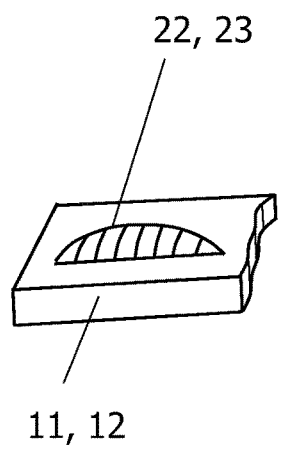
FIG. 4c is a detail of a second embodiment of a sliding edge.
Figure 4D:
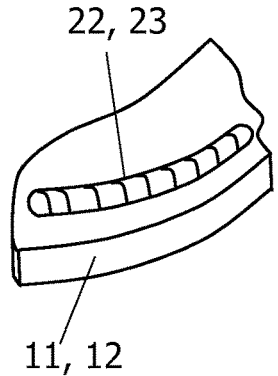
FIG. 4d is a detail of a third embodiment of a sliding edge.

FIGS. 3a and 3b show some details of the spike or spike group. One of the tasks of the spike 20 is to allow local intrusion into the bone surface upon actuation of the pulling mechanism 8 while minimizing damage to the bone and tissue. After assembly, the spike 20 placed in the bone 1 results in a reliable positioning of the bone clamp 2 at the spike site. Second, the thus fixed spike 20 defines a center of rotation about which the bone clamp 2 can rotate during the fastening operation. The rotation about the spike 20 is essential to allow the bone clamp 2 to move to a stable position and orientation by manipulation of the sliding edges 22, 23.

The penetration of the spike into the bone surface and the rotation about the center of rotation are coupled processes. Two or more spikes 20 forming a spike group may be provided instead of a single spike 20 as shown in FIG. 3b. Instead of or in addition to the spike or spikes 20, other elements can be attached, which allow a fixation on the bone. In particular, a spike has the property of penetrating the bone surface.

The spike 20 thus remains stationary in the bone 1 during the attachment process of the bone clamp 2 and during the release process of the bone clamp 2. Depending on the bone surface and expected bone hardness, as well as the bone geometry, a flat design, e.g. with a roughened surface may be provided. In addition to the spike 20, the first clip 11 may also have a sliding edge to allow the occlusion of the bone on both sides.

FIGS. 4a, 4b, 4c, 4d show some details of sliding edges 22, 23, which may in particular be formed as cutting edges, which come into contact with the bone surface. The tasks of the sliding edges 22, 23 are, in analogy to the spike 20, the local penetration into the bone surface when the pulling mechanism 8 is actuated, with the least possible impairment of the bone and the tissue. However, during attachment, the bone clamp may move locally in the direction of arrow 30 of the sliding edges 22, 23 over the bone surface. The penetration and displacement of the sliding edges 22, 23 are generally coupled operations. A plurality of parallel sliding edges 22, 23 may be provided instead of a respective sliding edge 22, 23. The length and sharpness of a sliding edge 22, 23 is specifically matched to the bone onto which the bone clamp is to be applied. The sliding edges 22, 23 may have a straight course or may be curved inwardly or outwardly. By the term "a straight course" it is meant in particular that the course of the edge, cutting edge or rib is formed as a straight line. An inward or outward curvature can be understood as a concave or convex curvature of the edge, cutting edge or rib. Especially for an application of the bone clamp on the femoral neck 4 a very high bone hardness is expected, so that in this case a sharp-edged design of the sliding edges 22, 23 may be advantageous, for example in the form of a blade. An embodiment with two sliding edges 22, 23 is advantageous for the application of the bone clamp on the right or left side of the femur. Depending on the side, the sliding edges come into contact with the bone from a slightly different direction, in particular two blades can be designed so that they lie in an optimal position relative to the bone, which also depends on the leg side on which the bone clamp is to be mounted. Depending on the bone geometry and hardness, it may be sufficient if the sliding edges have a blunt edge, an elongate rib or even a smooth surface, which lets the first and second clip 11, 12 slide in the closing direction along the bone. According to this embodiment, the closing direction substantially corresponds to the plane of the drawing, wherein the plane of the drawing spans the plane in which all fastening points are arranged on the bone. That is, in a direction that is normal to the drawing plane, no sliding can be performed. An attachment site can also be understood to be an area of the bone surface in which a contact of the sliding edge with the bone surface takes place, that is to say a contact between the bone surface and the sliding edge. Depending on the roughness of the surface of the sliding edge, the static friction may be sufficient to ensure a firm grip of the sliding edge on the bone surface. Thus, a point of attachment can also be understood as a point of contact which prevents that the position of the bone clamp from changes relative to the bone.

Figure 5:
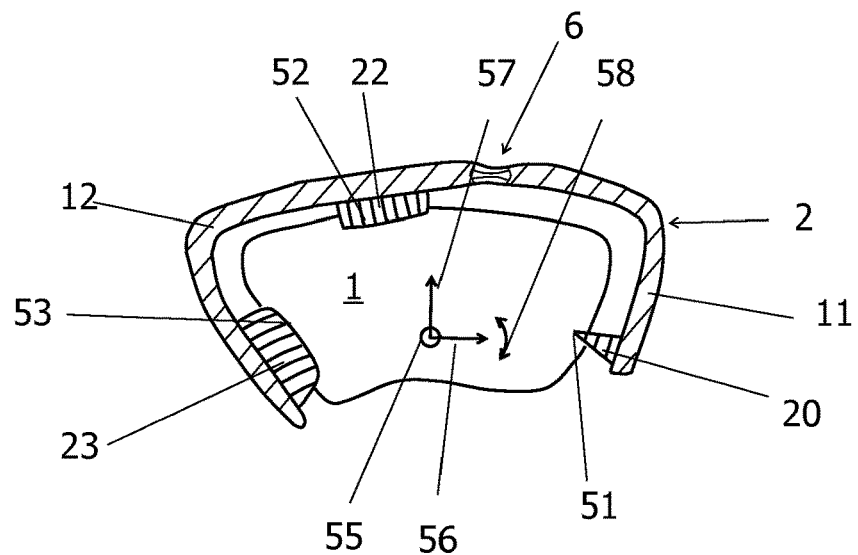
FIG. 5 is a side view of a fourth embodiment of a bone clamp.

FIG. 5 shows a view of a bone clamp according to a fourth embodiment, which contains some details regarding rotation and translation of the mounted bone clamp 2 with respect to the bone 1. The bone clamp 2 abuts the bone at three points, namely at the attachment location 51 through the spike 20, at the attachment location 52 through the sliding edge 22 and at the attachment location 53 through the sliding edge 23. The arrangement of the three attachment locations 51, 52, 53 prevents a rotation about the bone axis 55 and a tilting of the bone clamp 2 about both axes 56 and 57 which are perpendicular to the bone axis 55.

The bone axis 55 is positioned perpendicular to the plane of the drawing, as shown in FIG. 5. It is important that the spike 20 prevents any rotation of the attached bone clamp 2 about the bone axis 55 in the bone surface. Secondly, the three attachment locations 51, 52, 53 prevent translational movements parallel to the three axes 55, 56, and 57.

If the spike 20 is replaced by a sliding edge 22, 23, for example, an edge or cutting edge, the angle of rotation 58 about the bone axis 55 is less secured, but may be sufficiently secured depending on the bone cross-section. If a sliding edge 22, 23 is replaced by a spike 20 or all sliding edges 22, 23 replaced by spikes 20, the bone surface may be bruised when contracting the bone clamp.

In principle, a spike 20 and the two sliding edges 22 and 23 are sufficient to prevent rotations and translations of the attached bone clamp. The local forces on the bone surface and tissue, such as muscle attachments, can be reduced by increasing the number of spikes or spike groups 20 or the blades or blade combinations 22, 23 or by the curved shape of the sliding edges 22, 23, for example according to the embodiments shown in FIGS. 3a, 3b and 4a, 4b, 4c, 4d.

The cross section of the bone clamp 2 is increased or widened by increasing the number of spikes 20 and sliding edges 22, 23. Thereby, the ergonomics of the manipulation of the bone clamp can increase.

The bone clamp 2 of FIG. 5 also differs from the previous embodiments in that the adapter 6 is partially flexible. In particular, the adapter may comprise an elastic material which allows for a change in the length of the first and second clips 11, 12 and/or a change in the angular orientation of the first and second clips 11, 12. The two clips 11, 12 can thus be formed as a first and a second clip element, which is part of the bone clamp 2. As a result, a bone clamp is obtained in a particularly simple design.

Figure 6:
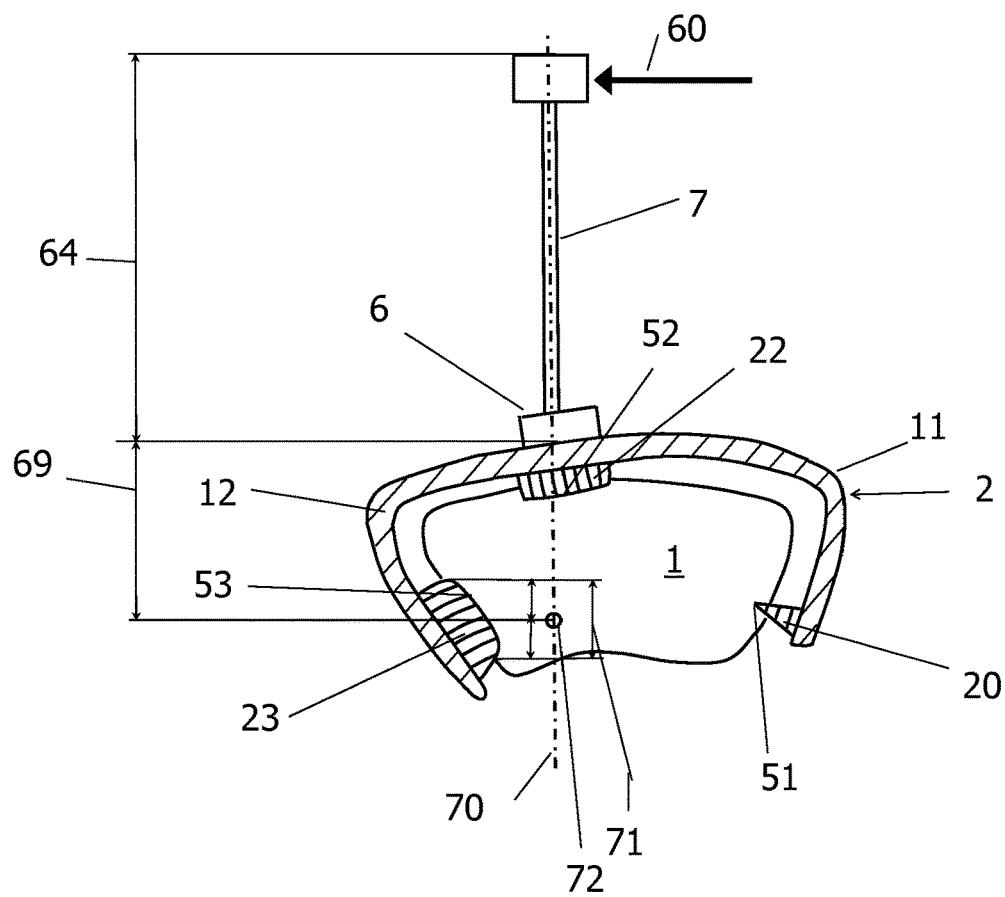
FIG. 6 is a side view of a fifth embodiment of a bone clamp.

FIG. 6 shows a side view of a fifth embodiment of a bone clamp 2. The first and second clips 11, 12 can be coupled via the adapter 6. FIG. 6 shows the forces acting on the three attachment locations 51, 52, and 53 by a force 60 acting on the measurement aid 7. The measurement aid 7 is connected to the attached bone clamp 2 by means of the adapter 6. The measurement aid 7 has a longitudinal dimension which corresponds to a first lever arm 64. The longitudinal dimension extends from the end of the measurement aid 7 to the surface of the second clip 12 in the point where the longitudinal axis impinges on this surface. The longitudinal dimension of the measurement aid 7 is measured along a longitudinal axis 70. The longitudinal axis also extends through the adapter 6. The projection of the attachment location 53 onto the longitudinal axis 70 results in a projection length 71 in the direction of the longitudinal axis. The projection length 71 has a path center point which is obtained by dividing the projection length 71 into two halves. This path center point corresponds to the lever end point 72 for the second lever arm 69 of the bone clamp 2 with respect to the longitudinal axis 70. The length ratio of the first lever arm 64 to the second lever arm 69 of the bone clamp 2 is preferably a maximum of five. That is, the first lever arm 64 is a maximum of five times longer than the second lever arm 69. The force acting on the three attachment locations 51, 52, 53 on the bone 1 decreases, if the length of the second lever arm 69 of the bone clamp 2 increases with respect to the first lever arm 64 of the measurement aid 7, that is, the smaller the aspect ratio is. An aspect ratio of at most 2 has turned out to be particularly advantageous.

Figure 7:
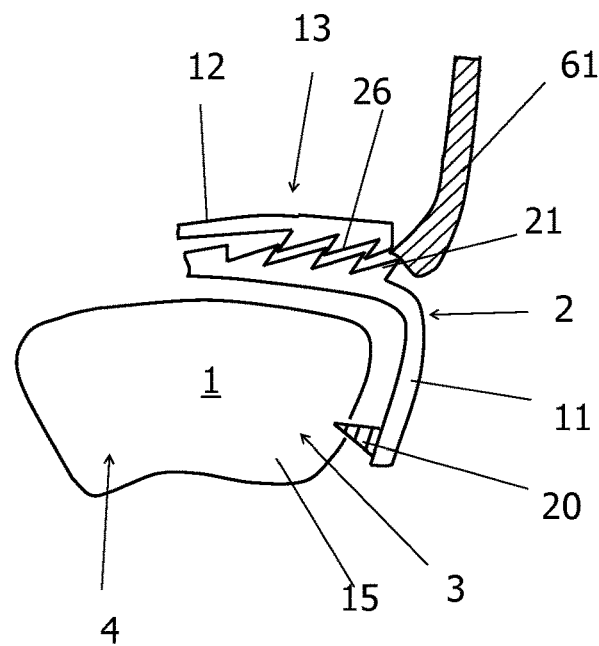
FIG. 7 is a device for releasing a locking mechanism for a bone clamp.

FIG. 7 shows an embodiment of a release mechanism to release the attachment of the bone clamp 2 on the bone again. The release mechanism according to the present embodiment includes a lever device 61. The lever device 61 is used to release the locking mechanism 13. For example, the engagement of the teeth of the sawtooth-like structures 21, 26 is released by means of the lever device 61. The lever device 61 is inserted between the sawtooth-like structures 21 located on the first clip 11 and the sawtooth-like structures 26 located on the second clip 12, whereby the spacing of the sawtooth-like structures 21 of the first clip 11 from the sawtooth-like structures 26 of the second clip 12 is increased. As a result, their teeth move out of engagement, so that the first clip 11 is slidable again relative to the second clip 12.

In FIG. 7, the first and second clip 11, 12 are not fully shown, for the pulling mechanism 8, for example, reference is made to the illustration of FIG. 2. Optionally, an inadvertent release can be prevented by a cover of the clip portion containing the locking mechanism 13, which is not shown in the figure. It is also conceivable to integrate the release mechanism and the pulling mechanism into an instrument.

Figure 8:
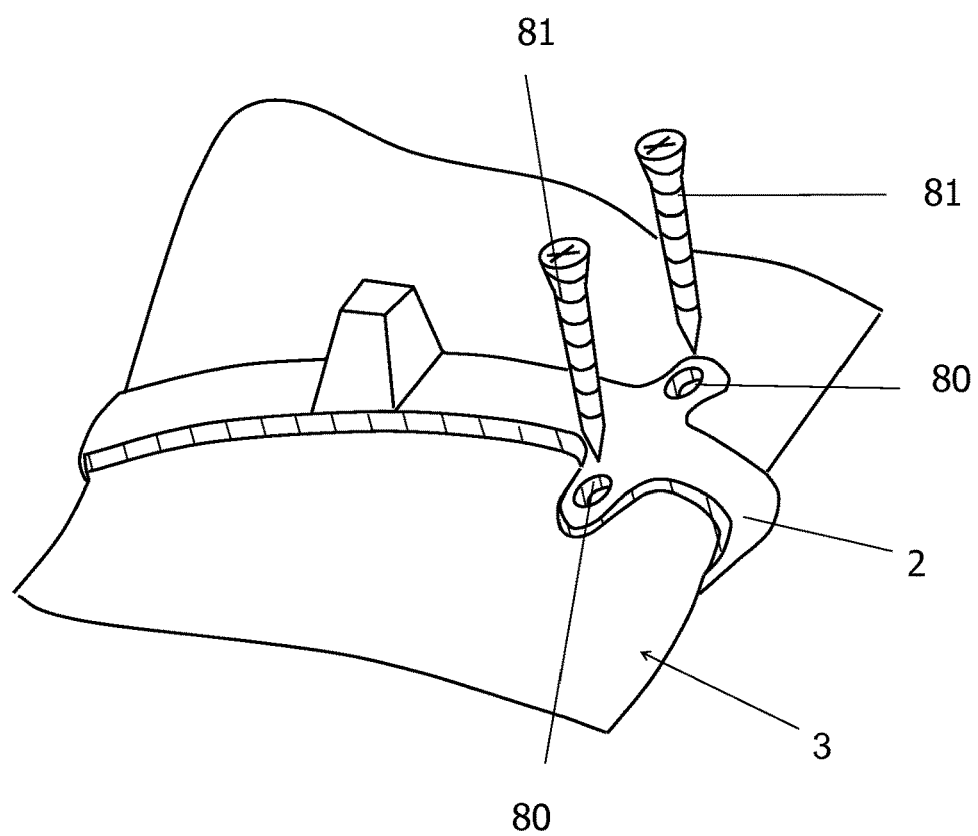
FIG. 8 is side view of a sixth embodiment of a bone clamp.

FIG. 8 shows a side view of a sixth embodiment of a bone clamp 2. FIG. 8 shows an option for an additional fixation of the bone clamp 2 fastened on the bone by a screw connection through eyelets 80 provided for this purpose. According to a particularly favorable variant, bone screws 81 are used, for example a head locking screw, which allows a defined orientation and positioning of the fastened bone clamp 2. When using the bone screws, it must be ensured that the bone screws used do not prevent the insertion of the implant. The bone clamp 2 which is according to this embodiment configured as a femoral clip is equipped with two eyelets 80, wherein preferably only one of these two eyelets 80 depending on location on the leg is used.

Figure 9A:
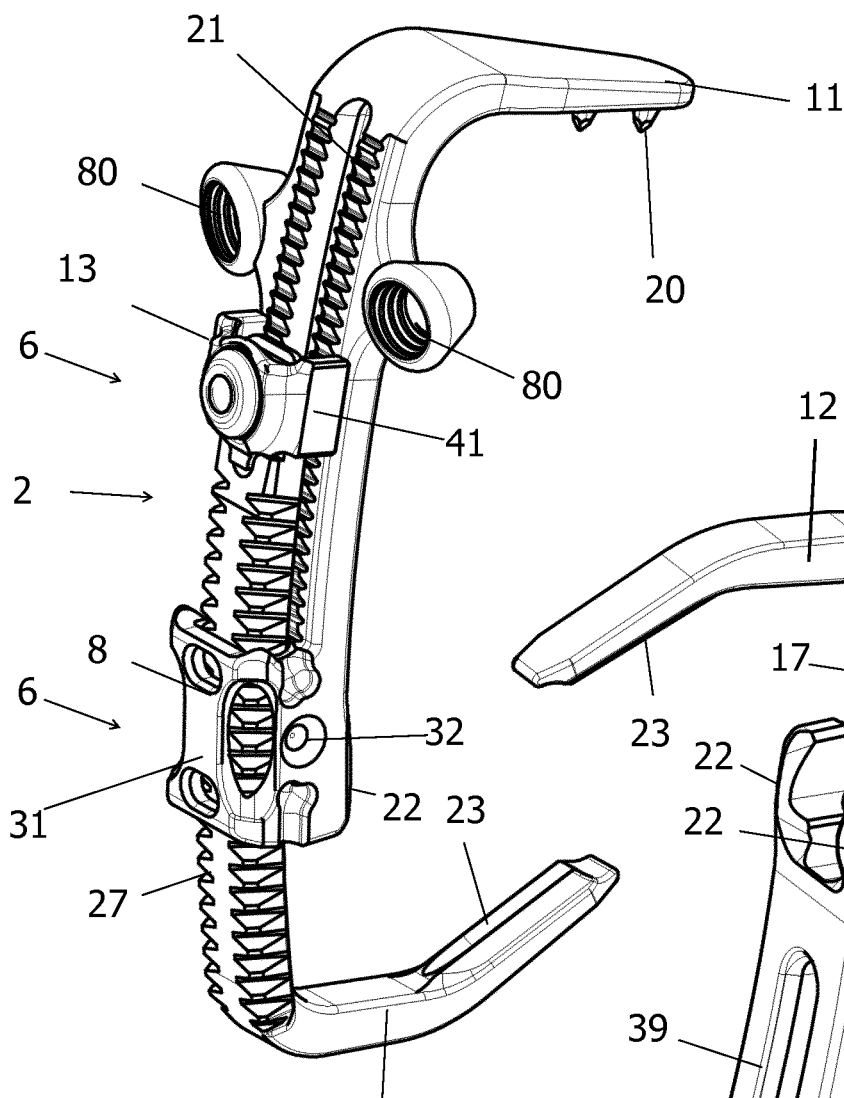
FIG. 9 is a view of a seventh embodiment of a bone clamp.
FIG. 9b is a further view of a seventh embodiment of a bone clamp.
FIG. 9c is a longitudinal section through a bone clamp according to a seventh embodiment.
Figure 9B:
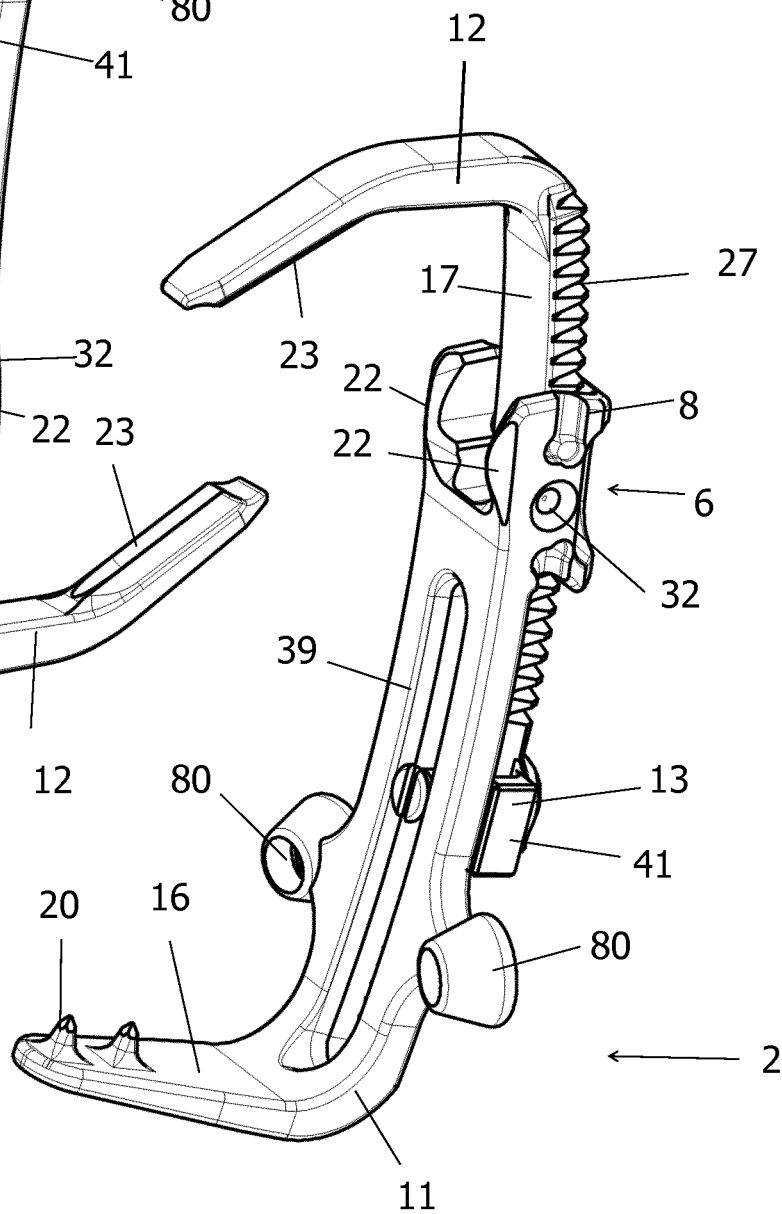

FIGS. 9*a* and 9*b* show a bone clamp 2 according to a seventh embodiment. The bone clamp 2 may contain a stainless steel. In particular, the bone clamp 2 may contain a surgical steel or preferably consist of surgical steel. The bone clamp 2 for attaching a measurement aid 7 to a bone comprises a first and a second clip 11, 12 and an adapter 6. The adapter 6 comprises a pulling mechanism 8 and a locking mechanism 13. The position of the first clip 11 relative to the second clip 12 can be changed by actuating the pulling mechanism 8. By actuating the locking mechanism 13, the position of the first clip 11 relative to the second clip 12 can be fixed. The first and second clips 11, 12 each have an inner face 16, 17, which is aligned in the direction of a bone surface of the bone 1. The first clip 11 includes on the inner face 16 one or more spikes 20 and a sliding edge 22 which is formed as a sliding edge pair. The second clip 12 includes on the inner face 17 a sliding edge 23, which may be formed as a sliding edge pair.

The pulling mechanism 8 is not fully shown in FIG. 9*a* or FIG. 9*b*, since the pulling mechanism 8 consists of several parts. The items are partially removable from the bone clamp 2. The first clip 11 has a guide element 31, which surrounds the second clip 12. The guide element 31 includes a first coupling element 32, which is intended to be connected to a second coupling element 33, which is shown in any one of FIG. 10, 11 or 12. The first coupling element 32 may be formed according to an embodiment as a bore with an internal thread.

The second clip 12 has a substantially straight clip portion and a curved clip portion. The straight clip portion is provided with a plurality of recesses, which can perform the function of a rack 27. According to the present embodiment, the straight clip portion on the outside has two edges along which the recesses are arranged.

Figure 10:
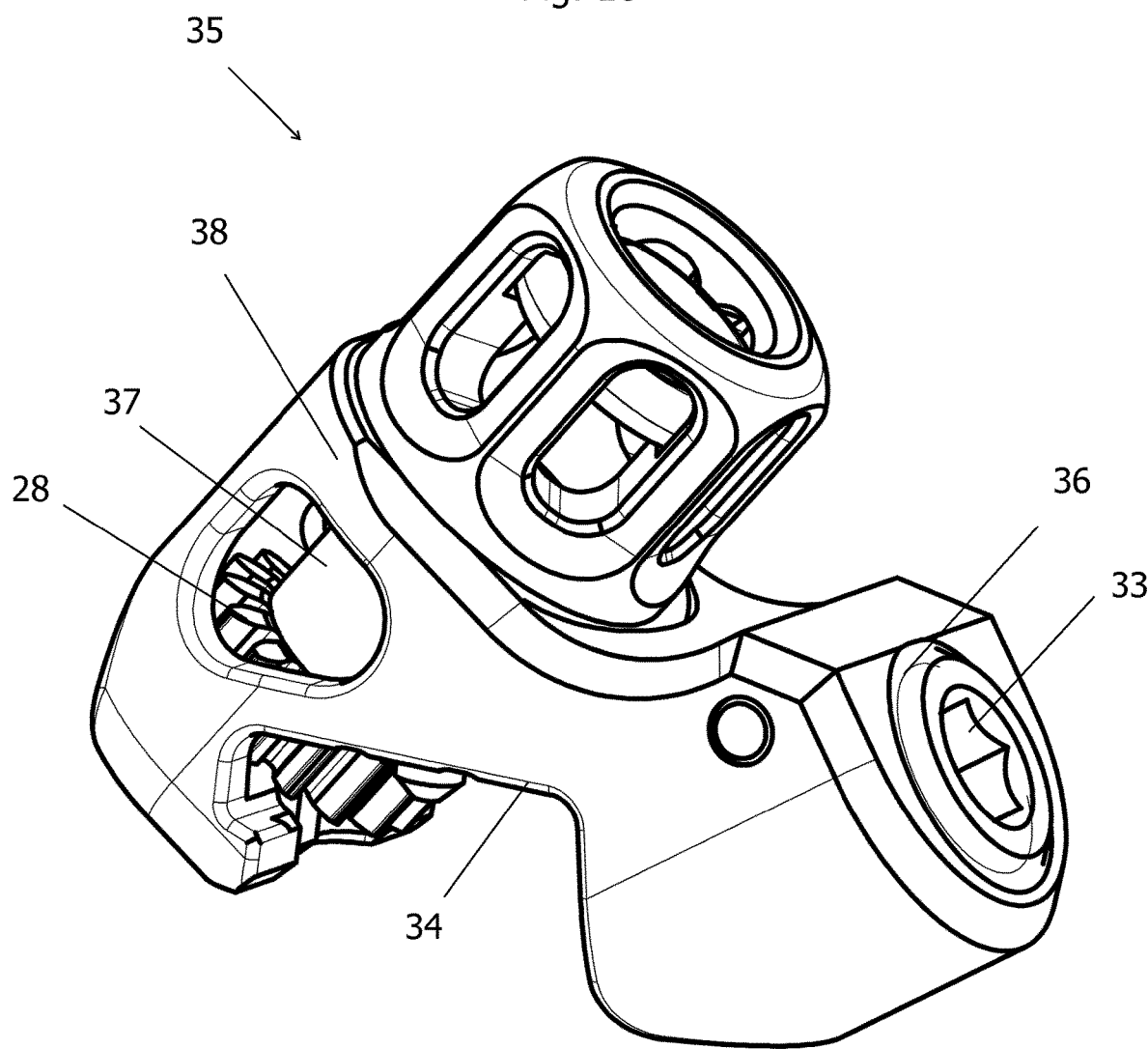
FIG. 10 is a view of an actuator assembly for a pulling mechanism.

The recesses have the shape of indentations that run along the two outer edges. The indentations are intended, for example, to receive the teeth of a gear 28 of an actuating arrangement 35, which is illustrated in FIG. 10. The recesses may, as shown in FIG. 9*a*, extend over the entire length of the straight clip portion, they could also be arranged only in a part of the straight clip portion, which is not shown in the drawing. According to the present embodiment, the first and second clips 11, 12 can thus be contracted almost to the extent that the length of the bone clamp 2 is not substantially greater than the length of the straight clip section of the second clip 12.

Each of the recesses has a first and a second recess wall. The recess wall according to this embodiment has a substantially triangular cross-section.

Because two edges of the straight clip portion each include a series of recesses, a gear 28 may be engaged with each of the two rows of recesses. The actuating arrangement 35 can thus be mounted in two different positions on the guide element 31. Depending on the desired application, thus, the actuating arrangement 35 can be placed in the appropriate position. This option can greatly facilitate the operation of the pulling mechanism 8 depending on the installation position of the bone clamp. The guide element 31 is thus symmetrical with respect to a longitudinal center plane.

The guide element 31 is arranged according to this embodiment at the end of a substantially straight clip portion of the first clip 11. In FIG. 9*a*, the outside of the substantially straight clip portion of the first clip 11 is shown, in FIG. 9*b*, the inside of the substantially straight clip portion of the first clip 11 is shown. The outside of the substantially straight clip portion of the first clip 11 has a first sawtooth-like structure 21. The outside of the substantially straight clip portion is thus provided over its entire width with the first sawtooth-like structure 21. According to the present embodiment, a slot 39 is arranged in the substantially straight clip portion of the clip 11. This slot 39 extends over a large part of the length of the substantially straight clip portion of the first clip 11. Thus, the substantially straight clip portion of the first clip 11 has two rows of first sawtooth-like structures 21.

The substantially straight clip portion of the first clip 11 also includes two projections, each having an eyelet 80 for a bone screw. With bone screws, which are passed through the two eyelets 80, the bone clamp 2 can be additionally attached to the bone. The eyelets 80 include an internal thread. The bone screws are not shown in this illustration.

The function of the first sawtooth-like structure 21 and the slot 39 is best seen in the illustration according to FIG. 9*c* and will be described here.

Figure 9C:
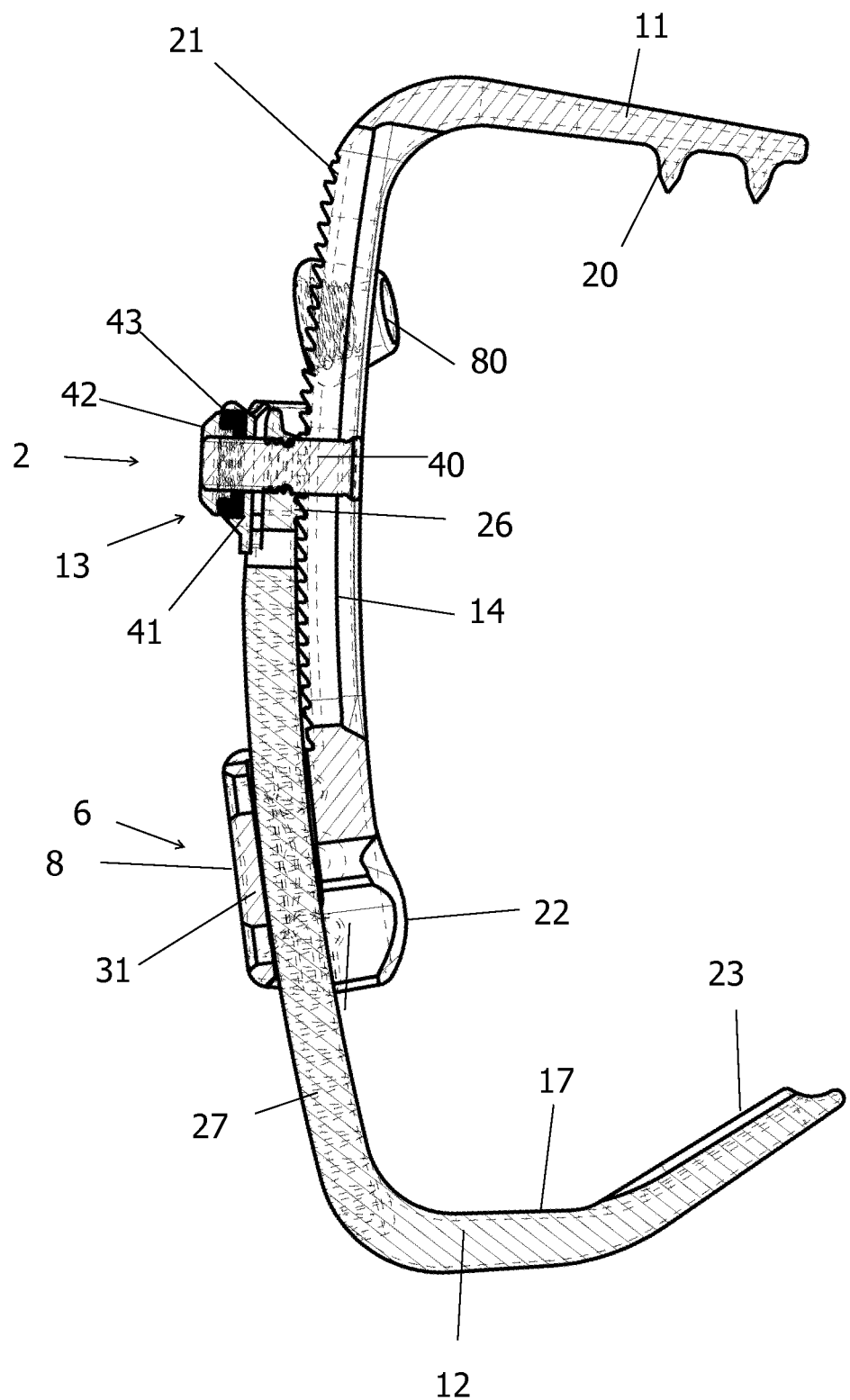

FIG. 9*c* shows a longitudinal section through the bone clamp 2 according to the seventh embodiment. The longitudinal section is laid along the longitudinal center plane of the first and second clip 11, 12. The longitudinal center plane may be formed according to this embodiment as a plane of symmetry. In particular, the teeth of the rack 27 may be formed mirror-symmetrically with respect to the longitudinal center plane. Also, the guide element 31 and the sliding element 41 may be mirror-symmetrical with respect to the longitudinal center plane.

Therefore, the recesses attached to the edges of the second clip are not visible in this illustration. The substantially straight clip portion of the second clip 12 may also have a slight curvature, which in FIG. 9*c* coincides with the curvature of a substantially straight clip portion of the first clip 11. The substantially straight clip portion of the second clip 12 can thus rest on the substantially straight clip portion of the first clip 11. The section through the substantially straight clip portion of the first clip 11 is placed such that the slot 39 is shown in section. The slot 39 extends according to this embodiment from the guide element 31 to the arc, in which the curved clip portion of the first clip 11 begins. The slot 39 is intended for receiving a pin 40, which is part of the locking mechanism 13. The locking mechanism 13 serves as in the previous embodiments to fix the position of the first clip 11 relative to the second clip 12. The pin 40 is attached to the end of the second clip 12. At the end of the second clip 12 may be provided a bore which serves to receive the pin 40. The end of the second clip 12 has on the inside a second sawtooth-like structure 26 which can engage with the first sawtooth-like structure 21 of the substantially straight clip portion of the first clip 11. The pin 40 can slide in the slot 39. It has a play in a normal direction to the direction of movement, so that it is movable by a few millimeters in the normal direction to the direction of movement. This mobility allows the release of the locking mechanism. The slot 39 has a shoulder 14 on which the bone-side end of the pin 40 can serve as a support. The bone-side end of the pin 40 may comprise an extension, such as a bead or a cone. In FIG. 9c, the locking mechanism is shown in its locked state, therefore, the extension of the pin 40 is not on the shoulder 14.

When the pulling mechanism 8 is actuated, the substantially straight clip portion of the second clip 12 slides over the substantially straight clip portion of the first clip 11. The feed direction of the substantially straight clip portion of second clip 12 is predetermined by the guide element 31 and the pin 40 sliding in the slot 39.

The second sawtooth-like structure 26 thus engages with the first sawtooth-like structure 21 of the substantially straight clip portion of the first clip 11. The teeth of the second sawtooth-like structure 26 engage the tooth roots of the first sawtooth-like structure 21. The second sawtooth-like structure 26 may comprise a single tooth, but may also have a plurality of teeth to reduce the flank pressure on the tooth flank of the counter tooth of the first sawtooth-like structure 21. Advantageously, the second sawtooth-like structure 26 may have at least 3 teeth, in particular the second sawtooth-like structure 26 may have at least 5 teeth. Each of the teeth may in particular have tooth flanks of different steepness. In particular, for the second sawtooth-like structure 26, the steepness of the flank, which is directed towards the end of the substantially straight clip portion of the second clip 12, may be less than the steepness of the flank, which is oriented towards the pulling mechanism 8.

In particular, for the first sawtooth-like structure 21, the steepness of the flank, which is directed towards the guide element 31, may be less than the steepness of the flank, which is aligned in the direction of the curved clip section of the first clip 11.

Therefore, the first sawtooth-like structure 21 latches with the second sawtooth-like structure 26 in any position set by the pulling mechanism 8.

The locking mechanism 13 thus includes the pin 40 as well as the second sawtooth-like structure 26. The second sawtooth-like structure 26 may be disposed on the end of the substantially straight clip portion of the second clip 12. The pin 40 may be received in a bore disposed in the end of the substantially straight clip portion of the second clip 12.

The pin 40 may be connected to a sliding element 41. The sliding element 41 forms a spring-mounted guide of the second clip 12 on the first clip 11. This spring-mounted guide has the task of making the entire closing path smooth in the loose state of the bone clamp 2. The two sawtooth-like structures 21, 26 are held apart by the sliding element 41 for this purpose.

The sliding element 41 has rails on the side facing the first clip 11. On these rails, the sliding element 41 can slide along the surface of the first clip 11. The pin 40 limits the free path of several centimeters.

In addition, the sliding element 41 may move perpendicularly to the clip surface along the pin 40. The play for this movement amounts in the normal direction to the clip surface a few millimeters, in particular about one millimeter.

The pin may have a nut 42 on the upper side, in which a spring element 43 is held, which rests on the outside of the sliding element 41. The nut 42 may be welded to the pin 40. The spring element 43 pushes the sliding element 41 against the outer surface of the end of the second clip 12. This pressure force is transmitted to the second sawtooth-like structure 26, which thus engages in the first sawtooth-like structure 21 of the first clip 11.

Thus, the substantially straight portion of the first clip 11 is pressed against the end of the second clip 12 by the spring element 43, so that the first sawtooth-like structure 21 engages in the corresponding second sawtooth-like structure 26. When the pulling mechanism 8 is actuated, the two sawtooth-like structures 21, 26 move along their less steep flank and compress the spring element 43. As soon as the next tooth root has been reached, the spring element 43 is released again so that the two sawtooth-like structures lock into one another. The end of the second clip can thus be moved away during the closing operation by the sliding movement of the first clip 11, whereby a progressive irreversible locking takes place, which leads to the desired attachment of the bone clamp 2 on the bone.

If the bone clamp 2 is to be removed from the bone again, the lock must be released with a specially developed unlocking tool. Any accidental unwanted loosening of the bone clamp 2 is thus excluded because the two sawtooth-like structures 21, 26 are held by the spring element 43 in engagement. By means of the unlocking tool, which may be formed as a lever device 61, as shown in FIG. 14a or FIG. 14b, the end of the second clip 12 can be moved in the direction of the nut 42, whereby the spring element 43 is compressed and the distance between the two sawtooth-like structures 21, 26 enlarged. As a result, the first and second sawtooth-like structures disengage, so that the pre-tensioning is released and the first clip 11 can be moved away from the second clip 12. The extension of the pin 40 rests on the shoulder 14 of the substantially straight clip portion of the first clip 11.

On the inner face 16 of the curved clip portion of the first clip 11, two spikes 20 are arranged. On the inner face 17 of the curved clip portion of the second clip 12, a sliding edge 23 is arranged. On the inner face of the substantially straight clip portion of the first clip 11, a sliding edge 22 is arranged. The spikes 20 and the sliding edge 23 and the sliding edge 22 are located on the bone surface and can also penetrate into the bone surface for better grip, whereby slipping of the bone clamp 2 can be securely prevented when the first and second sawtooth-like structures 21, 26 are in engagement position. When the release mechanism is actuated, the distance between the spikes 20 and the sliding edge 23 or the sliding edge 22 can also increase. The bone clamp 2 can be removed from the bone 1 without further injury to the bone surface. The sliding edge 23 may comprise a pair of sliding edges. The sliding edges of the pair may be arranged parallel to each other. The guide element 31 or the end of the first clip 11 may have a sliding edge 22. When the bone clamp 2 is mirror symmetric with respect to the longitudinal center plane, as shown in FIGS. 9a to 9c, also the sliding edge 22 may be formed as a pair of sliding edges.

An embodiment of an actuating arrangement 35 associated with a pulling mechanism 8 is shown in FIG. 10. The actuating arrangement 35 includes a second coupling element 33. The actuating arrangement 35 is placed on the guide element 31 for actuating the pulling mechanism 8. For this purpose, the actuating arrangement 35 has a recess 34 which can be positively connected to the guide element 31 (see FIGS. 9a-9c), so that the actuating arrangement 35 assumes a defined position with respect to the guide element 31.

The second coupling element 33 is connectable or connected to the actuating arrangement 35. According to an embodiment, the second coupling element 33 comprises a threaded pin or a locking screw which can be brought into engagement with the first coupling element 32 designed as a threaded bore or seat element according to this exemplary embodiment, in particular, it can be screwed or locked.

The second coupling element 33 may be received in a bore 36 of the actuating arrangement 35. The bore 36 may include a thread which is not visible in FIG. 10. The second coupling element 33 can be actuated with a coupling tool, for example a screwdriver.

The actuating arrangement 35 comprises a gear 28, which engages in the assembled state in the rack 27 mounted on the second clip 12. The gear 28 may be formed as a pinion. The gear 28 may be disposed on a shaft 37 which is rotatably supported in a housing 38. The shaft 37 may have a recess which is suitable for receiving a clamping tool 65. A clamping tool 65 may have a shape that matches the shape of the recess so that the clamping tool 65 can be inserted exactly into the recess of the shaft 37. By rotation of the clamping tool 65, the shaft 37 is rotated, which in turn initiates the rotation of gear 28 which is fastened to the shaft 37. At least a portion of the teeth of the gear 28 is engaged with the teeth on the rack 27, so that upon rotation of the gear 28, the rack 27 is displaced relative to the guide element 31, so that the first clip 11 can be moved relative to the second clip 12.

Figure 11:
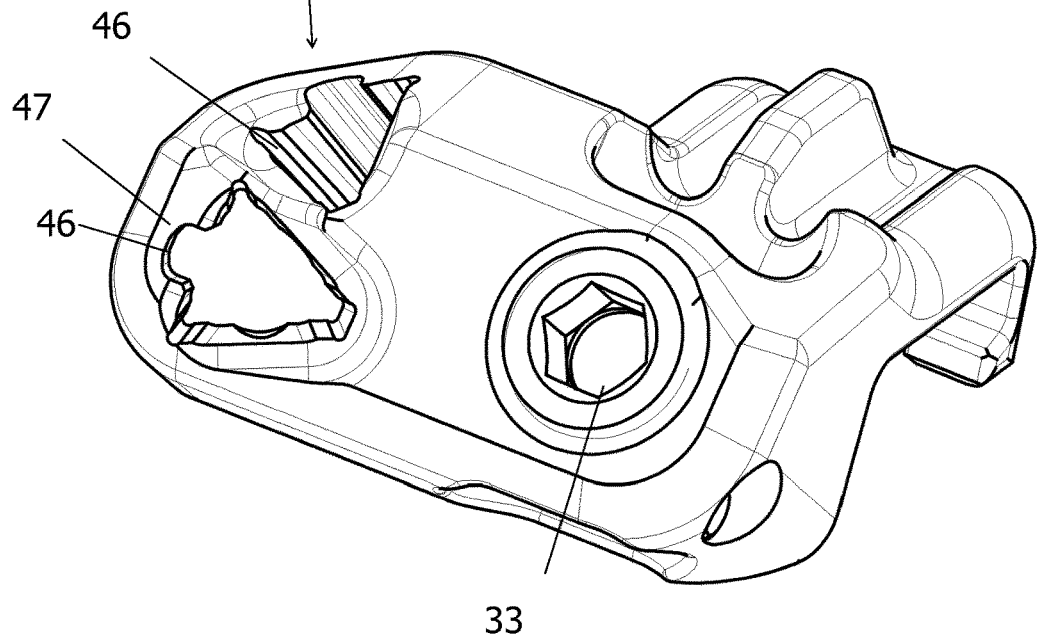
FIG. 11 is a view of a docking element for a measurement aid according to a first embodiment.

FIG. 11 shows a view of a first embodiment of a docking element 45 for a measurement aid. This docking element 45 can be connected to the guide element 31 after removal of the actuating arrangement 35. When the bone clamp 2 is mounted on the bone, that is, the locking mechanism 13 is in the installed position, the actuating arrangement 35 is no longer needed. The actuating arrangement 35 can be removed from the guide element 31 by releasing the second coupling element 33 with the coupling tool. The coupling element 32 located on the guide element 31 is now available in order to couple the docking element 45. Advantageously, the docking element 45 also has a coupling element for this purpose, which may correspond to the coupling element 33, so that the docking element 45 or the actuating arrangement 35 can optionally be connected to the guide element 31 located on the first clip 11. The docking element 45 has according to this embodiment two openings 46 which can be used as slots for a measurement aid. The openings 46 have according to this embodiment the same cross-sectional area, so that a measurement aid can be inserted into each of the two openings. The shape of the openings 46 is preferably corresponding to the shape of the plug element 76 of the measurement aid intended for connection to the docking element 45. An example of a measurement aid 7, which can be inserted into one of the openings 46, is shown in FIG. 15. An example of an associated plug element 76 is shown in FIG. 15.

The openings 46 are advantageously arranged in different orientation to each other on the docking element 45. According to this embodiment, they have a specific position relative to one another, so that the geometric relationship of the openings 46 to one another is defined. This means that the measurement aid can be arranged in different spatial directions and in different orientations. Due to the orientation of the openings, the orientation of the measurement aid 7 is precisely defined, so that their position in space is exactly defined. Of course, according to an embodiment, not shown, only a single opening 46 may be provided. According to another embodiment, not shown, more than two openings 46 may be provided.

According to the present embodiment, the openings 46 have a substantially triangular cross-sectional area. One of the sides of the triangle may have a recess 47, which is intended to receive a correspondingly shaped projection of the plug element 76 (see FIG. 15). The position of the measurement aid is known by the position of the opening 46 and the position of the recess 47.

Figure 12:
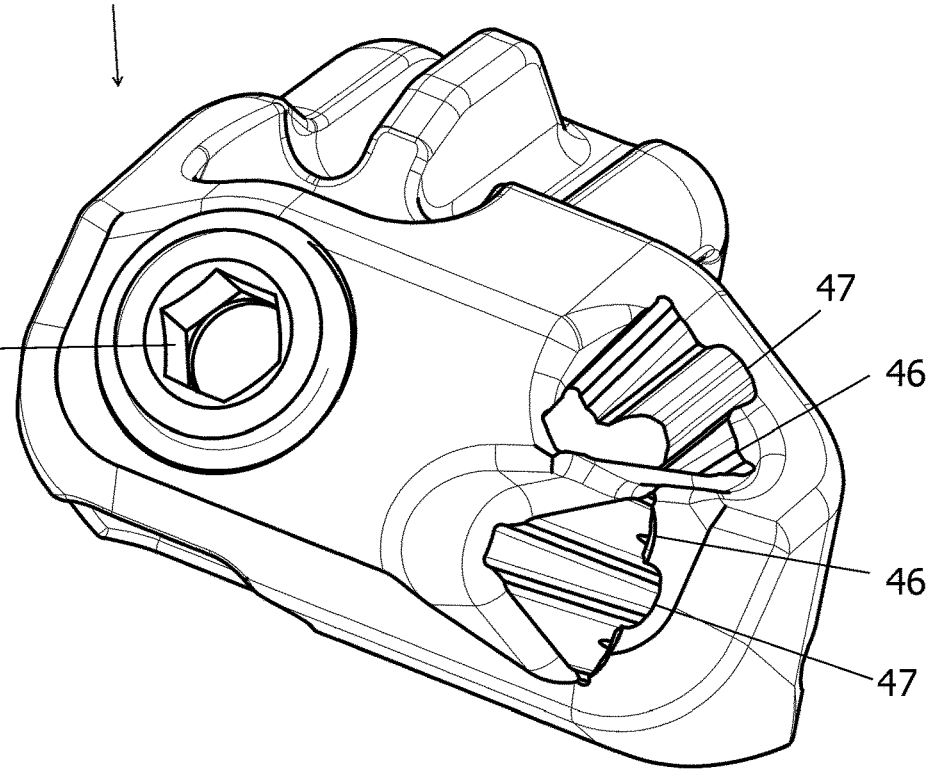
FIG. 12 is view of a docking element for a measurement aid according to a second embodiment.

FIG. 12 shows a view of a docking element 45 for a measurement aid 7 according to a second exemplary embodiment, which is configured mirror-symmetrically with respect to the docking element 45 of FIG. 11. The second coupling element 33 corresponds to the coupling element for the docking element 45. The openings 46 of FIG. 12 have the same shape as the openings 46 according to FIG. 11. In particular, the corresponding recess 47 in FIG. 12 can be configured in the same way as the recess 47 in FIG. 11.

FIG. 13 shows a view of a clamping tool 65. Advantageously, the gear 28 of the actuating arrangement 35 according to FIG. 10 can be actuated with the clamping tool 65. The clamping tool can also be used as a coupling tool when the coupling elements 33 have the same shape as the coupling element for the clamping tool 65 located on the shaft 37. According to the present exemplary embodiment, the clamping tool 65 can be different from the coupling tool, so that any incorrect manipulation is precluded.

The clamping tool and coupling tool may also be the same according to an embodiment, not shown. FIG. 14a shows a view of a lever device 61, which serves as an unlocking tool to release the locking mechanism 13 when the bone clamp 2 is to be removed from the bone 1. The lever device 61 is provided for manually releasing the locking mechanism 13. For this purpose, the lever device 61 has an engagement end 62, which is shown in detail in FIG. 14b. According to the present embodiment, the engagement end 62 is formed claw-shaped. The lever device 61 further has a handle 63.

FIG. 15 shows an exemplary embodiment of a holding element for a measurement aid 7. The holding element comprises a plug element 76, a rod element 74 and a connecting element 75. The plug element may include a locking element 73. The connecting element 75 serves to receive the measurement aid 7. The connecting element 75 may have a groove which is intended to receive the marking element.

It will be apparent to those skilled in the art that many other modifications are possible in addition to the described embodiments without departing from the inventive concept. Of course, it is possible to combine in particular the embodiments of the bone clamp and the system, in particular their first and second clip, adapter, measurement aids, pulling mechanisms or locking mechanisms with each other to achieve optimal properties of the bone clamp or the system for the appropriate application.

The inventive subject matter, therefore, is not to be restricted by the preceding description and encompasses the scope as laid out by the appended claims. Moreover, in interpreting both the specification and the claims, all terms should be interpreted in the broadest possible manner consistent with the context of the claims. In particular, the terms "comprise" and "include" should be interpreted as referring to elements, components, or steps in a non-exclusive manner, indicating that the referenced elements, components, or steps may be present, or utilized, or combined with other elements, components, or steps that are not expressly referenced. Where the specification or the claims refer to at least one of an element or compound selected from the group consisting of A, B, C . . . and N, the text should be interpreted as requiring only one element from the group, not a combination of A plus N, or B plus N, or any other combination of two or more elements or components of this group.

The invention claimed is:

1. A bone clamp for securing of a measurement aid to a bone comprises a first clip and a second clip and an adapter, wherein the adapter comprises a pulling mechanism and a locking mechanism, whereby a position of the first clip relative to the second clip can be altered by actuation of the pulling mechanism, wherein the position of the first clip relative to the second clip can be fixed by actuation of the locking mechanism wherein the first clip and the second clip each have an inner face which is oriented in a direction of the bone, wherein the first clip has one or more spikes on the inner face and wherein the second clip has a sliding edge on the inner face, wherein the second clip has a clip axis, wherein the sliding edge is arranged parallel to the clip axis, wherein the sliding edge is designed as a cutting edge extending parallel to the clip axis.

2. The bone clamp according to claim 1, wherein the sliding edge comprises a first sliding edge, the bone clamp further comprising a second sliding edge that is mounted on the first clip at a distance from the spike.

3. The bone clamp according to claim 2, wherein the first clip has a clip axis, and wherein the second sliding edge is arranged parallel to the clip axis.

4. The bone clamp according to claim 3, wherein the first and second sliding edges are parallel to the respective clip axes.

5. The bone clamp according to claim 3, wherein the first and second sliding edges and the spike lie in the same plane.

6. The bone clamp according to claim 3, wherein the first and second sliding edges enclose an angle smaller than 90° to each other.

7. The bone clamp according to claim 1, wherein at least one of the first and second clips is shaped to partially enclose the bone.

8. The bone clamp according to claim 1, wherein at least one of the first or second clips or the adapter is at least partially flexible.

9. The bone clamp according to claim 1, wherein the locking mechanism comprises first and second sawtooth-like structures disposed on the first and second clips and intended for mutual engagement.

10. The bone clamp according to claim 1, wherein the pulling mechanism comprises a gear disposed on the first clip and a rack disposed on the second clip, wherein the rack and the gear are intended for mutual engagement.

11. The bone clamp according to claim 10, wherein the gear is arranged detachably on the first clip.

12. The bone clamp according to claim 1, wherein the adapter contains a fastening device for a measurement aid.

13. The bone clamp according to claim 12, wherein the fastening device for the measurement aid or the measurement aid is removable from the first clip.

14. The bone clamp according to claim 1, wherein at least one eyelet for a bone screw on at least one of the first or second clip is provided.

15. The bone clamp according to claim 14, wherein the eyelet is adapted to receive a head locking screw.

16. The bone clamp according to claim 1, wherein a force of the first and second clips on the bone is adjustable by means of a torque measuring device.

17. The bone clamp according to claim 1, wherein a plurality of spikes form a spike group.

18. The bone clamp according to claim 1, wherein the sliding edge comprises a first sliding edge, the bone clamp further comprising a second sliding edge, wherein at least one of the first sliding edge or the second sliding edge includes a plurality of cutting edges, wherein the cutting edges of the sliding edge form a group of cutting edges.

19. The bone clamp according to claim 1, wherein a measurement aid is mounted on the adapter, wherein the measurement aid has a longitudinal dimension extending from a surface of the first or second clip to an end of the measurement aid and forms a first lever arm, wherein a second lever arm is formed from the surface of the first or second clip to a projection point of a track center of the sliding edge, and wherein a ratio of length dimensions of the first lever arm to the second lever arm is a maximum of five.

20. A system comprising a bone clamp for securing of a measurement aid to a bone comprises a first clip and a second clip and an adapter, wherein the adapter comprises a pulling mechanism and a locking mechanism, whereby a position of the first clip relative to the second clip can be altered by actuation of the pulling mechanism, wherein the position of the first clip relative to the second clip can be fixed by actuation of the locking mechanism wherein the first clip and the second clip each have an inner face which is oriented in a direction of the bone, wherein the first clip has one or more spikes on the inner face, wherein the second clip has a sliding edge on the inner face, wherein a measurement aid is mounted on the adapter, wherein the measurement aid has a longitudinal dimension extending from a surface of the first or second clip to an end of the measurement aid and forms a first lever arm, wherein a second lever arm is formed from the surface of the first or second clip to a projection point of a track center of the sliding edge, and wherein a ratio of length dimensions of the first lever arm to the second lever arm is a maximum of five.

* * * * *